(12) United States Patent
Gerlitz

(10) Patent No.: US 11,435,575 B2
(45) Date of Patent: Sep. 6, 2022

(54) OPTICAL CONFIGURATION FOR A LOW LEVEL LASER THERAPY DEVICE

(71) Applicant: Yonatan Gerlitz, Lev Hasharon (IL)

(72) Inventor: Yonatan Gerlitz, Lev Hasharon (IL)

( * ) Notice: Subject to any disclaimer, the term of this patent is extended or adjusted under 35 U.S.C. 154(b) by 505 days.

(21) Appl. No.: 16/680,771

(22) Filed: Nov. 12, 2019

(65) Prior Publication Data

US 2020/0150422 A1 May 14, 2020

Related U.S. Application Data

(60) Provisional application No. 62/760,655, filed on Nov. 13, 2018.

(51) Int. Cl.
*G02B 27/30* (2006.01)
*A61N 5/067* (2006.01)
*G02B 27/00* (2006.01)
*G02B 7/14* (2021.01)
(Continued)

(52) U.S. Cl.
CPC .......... *G02B 27/0025* (2013.01); *A61N 5/06* (2013.01); *G02B 1/11* (2013.01); *G02B 7/14* (2013.01); *G02B 27/30* (2013.01); *A61N 5/067* (2021.08); *A61N 2005/0651* (2013.01)

(58) Field of Classification Search
CPC .............. G02B 27/0025; G02B 27/30; G02B 27/0911; G02B 27/0916; G02B 19/0014; G02B 19/0052; A61N 5/00; A61N 5/06; A61N 5/067
See application file for complete search history.

(56) References Cited

U.S. PATENT DOCUMENTS

| 3,974,507 A | 8/1976 | Chemelli et al. |
| 6,392,813 B1 | 5/2002 | Reardon et al. |
| 9,358,402 B2 | 6/2016 | Gerlitz |

(Continued)

FOREIGN PATENT DOCUMENTS

| CN | 101916964 A * | 12/2010 |
| WO | 2014181196 A2 | 11/2014 |

OTHER PUBLICATIONS

Israel Patent Office (as ISA), "International Search Report" (Form PCT/ISA/210), PCT Patent Application No. PCT/IB2019/059752; dated Feb. 20, 2020; pp. 1-9.

(Continued)

*Primary Examiner* — Ryan D Howard
(74) *Attorney, Agent, or Firm* — Rod D. Baker

(57) ABSTRACT

A system and method to improve astigmatism correction and collimation of a laser beam generated by a diode in a low-level laser therapy system, but without using a complex optical configuration. A first divergent lens is a cylindrical lens. The divergence of the first lens is applied in the direction in which the diode's beam has relatively small divergence. The first lens creates divergence in the beam in a first axis, which divergence approximates the divergence in the perpendicular second axis. This first axis divergence corrects the astigmatism in the optical system of the therapy apparatus. The therapy apparatus thus can emit a beam with an elliptical cross-section with an axes ratio of less than 2:1, despite a high axes ratio of the beam originated by the diode. A second lens of the system and method is a collimating lens with elliptical shape adapted to maximize emitted beam collimation.

12 Claims, 2 Drawing Sheets

(51) Int. Cl.
    *A61N 5/06*    (2006.01)
    *G02B 1/11*    (2015.01)

(56) References Cited

U.S. PATENT DOCUMENTS

| | | |
|---|---|---|
| 9,946,082 B2 | 4/2018 | Gerlitz |
| 2013/0317571 A1 | 11/2013 | Gerlitz |
| 2016/0103328 A1 | 4/2016 | Heinrich et al. |

OTHER PUBLICATIONS

Israel Patent Office (as ISA), "Written Opinion of the International Searching Authority" (Form PCT/ISA/237) PCT Patent Application No. PCT/IB2019/059752; dated Feb. 20, 2020; pp. 1-4.

\* cited by examiner

OPTICAL CONFIGURATION FOR A LOW LEVEL LASER THERAPY DEVICE

CROSS-REFERENCE TO RELATED APPLICATIONS

This application claims the benefit of U.S. Provisional Patent Application Ser. No. 62/760,655 entitled "Improved Optical Configuration for Low Level Laser Therapy Device," filed on 13 Nov. 2018, the entire disclosure of which is hereby incorporated by reference.

BACKGROUND OF THE INVENTION

Field of the Invention

This invention relates to providing low-level laser therapy to patients, particularly to the optical configurations for apparatuses for providing such therapies, and specifically to a simply configured optical arrangement for improving astigmatism correction, and collimation, of a laser beam in a low-level laser therapy system.

Background Art

Issued patents relating to low-level laser therapy (LLLT) apparatus configurations include U.S. Pat. No. 9,358,402 to Gerlitz and U.S. Pat. No. 9,946,082 to Gerlitz. The system of U.S. Pat. No. 9,358,402 employs a single lens, and its shape corresponds to the original dimensions of a laser diode beam and may make partial correction to laser diode astigmatism by using a toroid lens. The system of the U.S. Pat. No. 9,946,082 employs two cylindrical lenses, which corrects the laser astigmatism and then uses beam expander to expand the beam and to improve collimation of the beam. The entireties of the aforementioned patents are hereby incorporated herein by reference.

SUMMARY OF THE INVENTION

The present system and method improve astigmatism correction and collimation of a laser beam in a low-level laser therapy system, but advantageously without using a complex optical configuration. Laser energy with therapeutic characteristics is generated by a laser diode known in the art. To achieve the object and advantage of the invention, a first divergent lens of a beam expander is configured as a cylindrical lens, and the divergence of this first lens is applied in the direction in which the laser diode's beam has relatively small divergence. Thus, the lens is designed to create divergence in the beam in a first axis that will more closely approximate the divergence in the second, perpendicular axis. This creation of a divergence in the first axis corrects, at least partially, the astigmatism in the optical system of the low-level laser therapy apparatus. The therapy apparatus thus emits a beam with an elliptical cross-section with an axes ratio of less than 2:1 (i.e., of the major axis versus minor axis of the ellipsis of the beam's cross section), despite that the diode may emit an original beam with an axes ratio exceeding 4:1. A second lens of the beam expander according to the present system is a collimating lens with elliptical shape, preferably an aspheric lens adapted to maximize emitted beam collimation.

This system configuration achieves about the same ultimate performance as that of U.S. Pat. No. 9,946,082, but with the significant advantage of simplicity, by using only two lenses. The two lenses serve to correct astigmatism in addition to expanding the emitted beam.

The second (i.e. front) collimating lens is changeable by the user. Interchangeable lenses with different apertures (having different focal lengths and different positions) improve the versatility and adaptability of the overall system.

The elements of the figures are not necessarily to scale, either between views or within a single view.

DETAILED DESCRIPTION OF THE INVENTION

The present system and method address the problem that many, if not most, of the laser diodes used in portable hand-held low-level laser therapy devices are diodes that emit an elliptical beam with a high ellipse axes ratio. For example, many such diodes generate a beam with an elliptical cross section in which the major axis of the ellipse is four times longer than the length of the minor axis, i.e., an axes ratio exceeding 4:1. Such a high axes ratio is undesirable for a beam to be applied to a patient in a low-level laser therapy context. The output of the laser diode diverging in an asymmetrical pattern increases the difficulty of collimating the beam to a shape and size useful in therapy.

The present system and method accordingly provides an optical arrangement for reducing the axes ratio of the beam initially emitted by the generating laser diode. The optical system configuration employs two lenses; in a possible embodiment, it employs two and no more than two lenses in the optical train. A first lens, which receives the beam as emitted from the laser diode, is a cylindrical diverging lens. The cylindrical lens in effect "circularizes" the beam. An attempt to collimate with spherical optics a beam with a high axes ratio would result in collimation in one direction only, with a diverging or converging beam in the other direction. With a cylindrical lens in the optical train of a low-level laser therapy device, the beam is collimated in one dimension to decrease the elliptical axes ratio of the beam ultimately applied to the patient.

Figure 1:
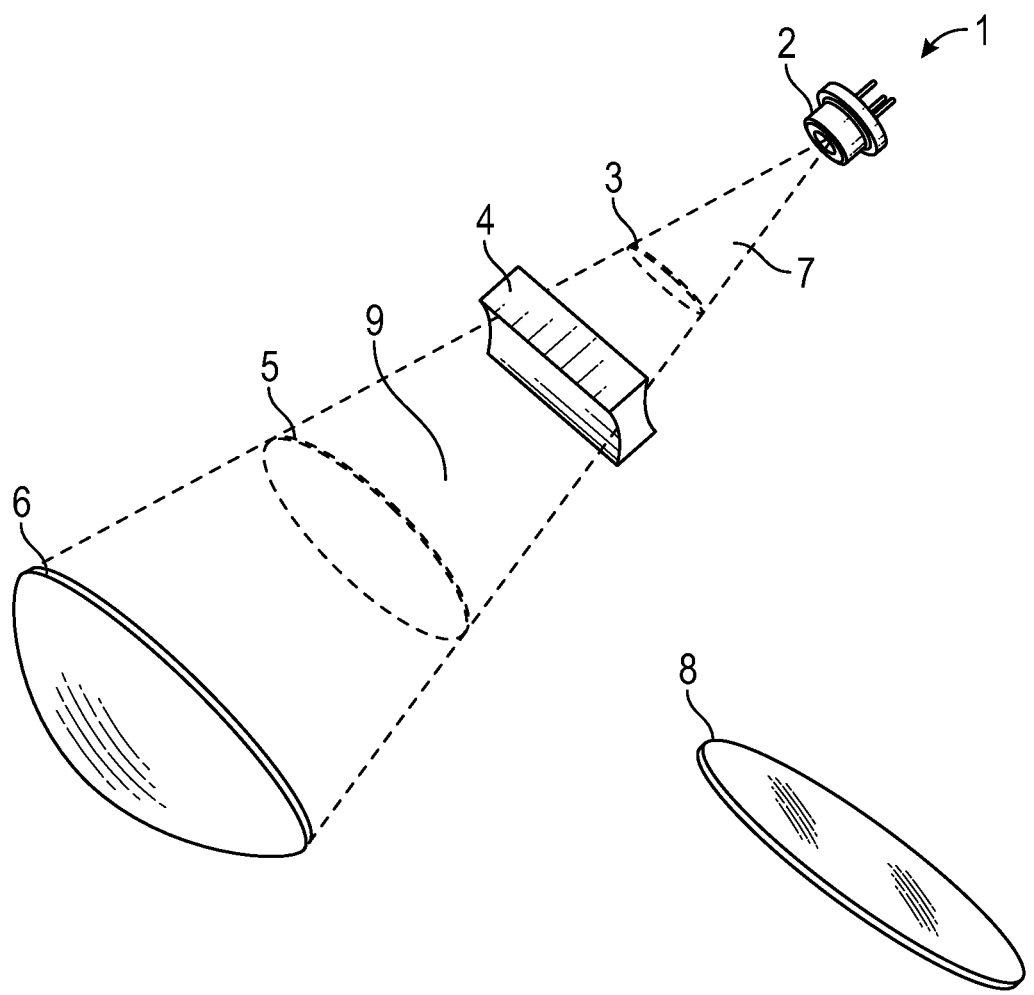
FIG. 1 is a diagrammatic depiction of the optical system according to the present disclosure, showing the laser diode which generates the laser beam, and showing the system configuration that alters the beam.

Attention is invited to the drawing figure, FIG. 1. A preferred embodiment of an optical system 1 according to the present disclosure may be adapted for use in a low-level laser therapy (LLLT) apparatus, such as that of U.S. Pat. No. 9,358,402, or that of U.S. Pat. No. 9,946,082. More particularly, the system disclosed herein is useable, for example, in the hand-held laser therapy apparatus seen in FIGS. 5A-5C of U.S. Pat. No. 9,946,082. The optical system of FIG. 1 of the present disclosure can be adapted for installation and use within such a device. The system 1 includes an optical train having a laser diode 2, a first lens 4, and a second lens 6. The laser diode 2 emits an initial beam 7 of light with an elliptical cross-section, this first beam's cross-section ellipsis 3 having a major axis and a minor axis according to conventional geometric terminologies. For a typical diode 2, the axes ratio (major axis to minor axis) of the axes of the ellipse 3 of the first beam cross-section exceeds 4:1. It is desired to reduce this ratio so to regulate astigmatism and thereby improve the performance of the overall system.

The first lens 4 is a cylindrical diverging lens. First lens 4 is located and oriented in the system to increase the divergence of the first beam 7 (with cross section 3, initially emitted from the diode 2) in the minor axis (that is, where the divergence is lower). The first lens 4 features cylindrical optics for diverging the beam in one axis, as known in the art. The length dimension of the minor axis of the first elliptical cross section 3 of the original beam 7 thus is increased, toward the length dimension of the major axis of ellipsis 3, approximately to match the initial degrees of divergence of the major axis—and thus to correct the astigmatism of the first beam 7. As seen in FIG. 1, the lens 4 is oriented such that at least one of its cylindrical axis/axes are approximately parallel to the major axis of the of the first beam's cross-section ellipsis 3.

After the beam 7 has passed the first cylindrical diverging lens 4, the manipulated beam 9 has a second beam cross-section 5. Because of the beam manipulation by the first lens 4, this elliptical second beam cross-section 5 has a minor axis dimension closer in length to the length of the major axis of this second ellipsis 5. In a preferred embodiment, the first lens 4 adjusts the beam axes ratio to a second axes ratio, in the second beam cross section 5, of about 2:1 or lower.

The second lens 6 is a conventional collimating lens having an elliptical shape substantially proportional to the shape of the beam 9 transmitted from the first lens 4. The cross-sectional dimensions (in a plane perpendicular to the optical axis of the second beam 9 of the second lens 6) is at least equal to the cross-sectional dimensions of the incident second beam, and preferably substantially matches or corresponds in size and shape to the cross-section of the incident beam. Lens 6 collimates the incident beam 9 received from the first lens 4, so that the beam emergent from the second lens 6 is well-collimated for beneficial use in the LLLT apparatus. The second lens 6 preferably is an aspheric lens to eliminate spherical aberration, and preferably providing diffraction-limited spot sizes for the beam.

An advantage of the invention is that the second lens may be interchangeable with another second lens 8. A user accordingly may remove the second lens 6 and replace it with another lens 8 selected to adapt the system 1 to the particular intended use, or functional context, of the system. In a preferred embodiment of the system 1, both the lenses 4 and 6 (or 8) preferably are made by plastic injection and coated with anti-reflection coating for the bend of the laser diode wavelength.

Figure 2A:
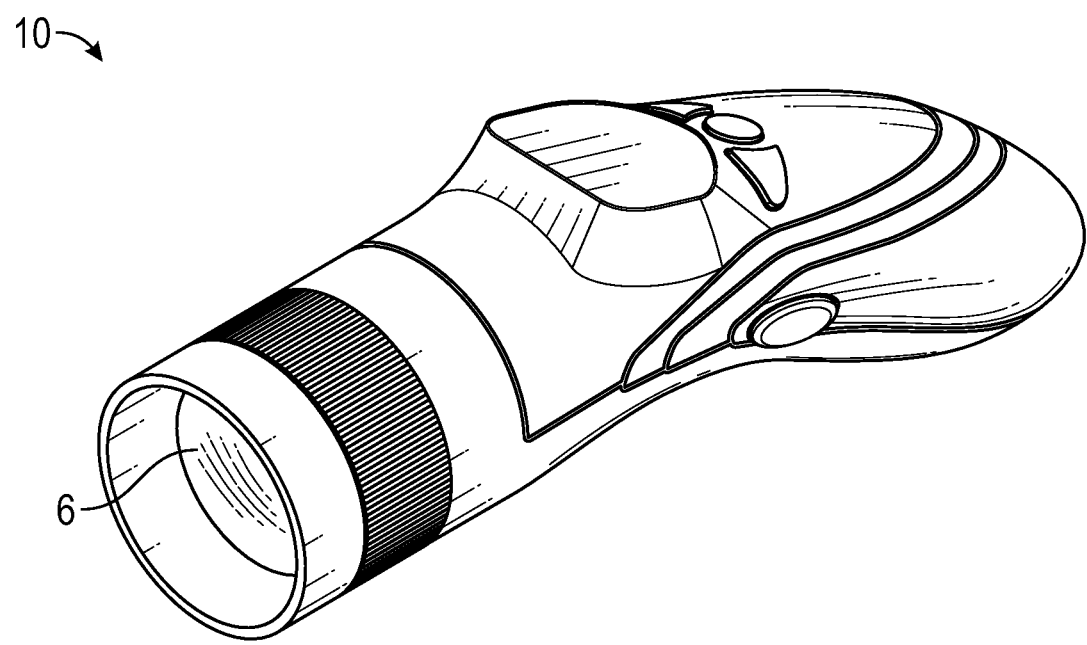
FIG. 2A is a perspective view of a portable hand-held low-level laser therapy apparatus in which the optical system of FIG. 1 is incorporated, showing a second lens from which the therapeutic beam is emitted toward the patient.
Figure 2B:
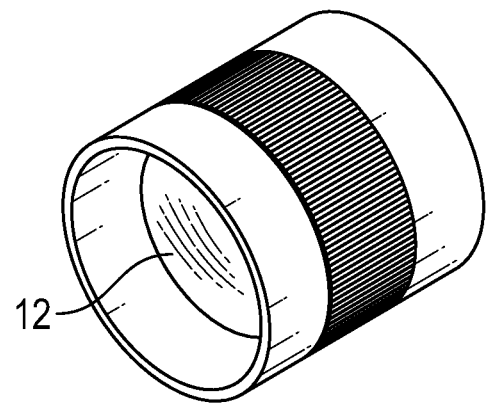
FIG. 2B is a perspective view of an alternate second lens which may be interchanged with the second lens shown in FIG. 2A.

FIG. 2A depicts a hand-held low-level laser therapy appliance 10 within the housing of which the optical assembly 1 of the present disclosure may be installed. FIG. 2A shows the collimating lens 6 in an assembly removably attached to the LLLT apparatus 10. FIG. 2B illustrates that some other second collimating lens 12 may be provided (e.g., corresponding to lens 8 in FIG. 1). The second lens 6 assembly may be removed from the appliance 10 and replaced with another assembly with a second lens 12 having optical characteristics selected for the particular use to which the appliance 10 is to be put.

There is provided, therefore, a system 1 for generating an astigmatism-corrected beam having an elliptical cross-section shape emitted from a low-level laser therapy device 10. The system comprises a laser diode 2 for generating a first beam 7 with an elliptical cross section 3 having a low-divergence minor axis and a high-divergence major axis; a first-divergence cylindrical lens 4 which increases a divergence of the low-divergence minor axis toward the divergence of the high-divergence major axis, the cylindrical lens 4 thereby transmitting a second beam 9 with a second elliptical cross section 5; and a first collimating lens 6 for receiving and collimating the second beam 9. By these means the collimating lens 6 emits an emitted beam having an emitted beam elliptical cross section with a minor axis length and a major axis length, and wherein the ratio of the major axis length to the minor axis length is less than 2:1.

As evident from the foregoing, there also is provided a method for generating an astigmatism-corrected beam having an elliptical cross-section shape emitted from a low-level laser therapy appliance 10, the method including the steps of: generating with a laser diode 2 a first beam 7 with an elliptical cross section 3 having a low-divergence minor axis and a high-divergence major axis; increasing with a first-divergence cylindrical lens 4 a divergence of the low-divergence minor axis toward the divergence of the high-divergence major axis, thereby transmitting with the cylindrical lens 4 a second beam 9 with a second elliptical cross section 5; receiving and collimating the second beam 9 with a first collimating lens 6; and emitting with the collimating lens 6 (and from the appliance 10) an emitted beam having an emitted beam elliptical cross section with a minor axis length and a major axis length, and wherein the ratio of the major axis length to the minor axis length is less than 2:1. In this method, the step of generating the first beam 7 includes generating the first beam with an initial beam elliptical cross section 3 with a minor axis length and a major axis length, in which the ratio of the initial beam elliptical cross section major axis length to the initial beam elliptical cross section minor axis length to be at least 4:1. The method may include the step of interchanging the first collimating lens 6 with a second, selected different, collimating lens 8.

As mentioned, an advantage of the present system and method is that astigmatism in a LLLT apparatus can be suitably corrected in a simple optical train consisting, in one preferred embodiment, of only two lenses, a first cylindrical lens and a second collimating lens. The need for two diverging lenses is eliminated. This advantage promotes use of the system in a physically compact hand-held LLLT apparatus, with relatively reduced manufacturing cost.

Although the invention has been described in detail with particular reference to these preferred embodiments, other embodiments may achieve the same results. In the previous description, specific details are set forth, such as specific materials, structures, chemicals, processes, etc., in order to provide a thorough understanding of the present invention. However, as one having ordinary skill in the art would recognize, the present invention can be practiced without resorting to the details specifically set forth. In other instances, well known principles of mechanics and physics have not been described in detail, in order not to unnecessarily obscure the present invention.

Only some embodiments of the invention and but a few examples of its versatility are described in the present disclosure. It is understood that the invention is capable of use in various other combinations and is capable of changes or modifications within the scope of the inventive concept as expressed herein. Modifications of the invention will be obvious to those skilled in the art and it is intended to cover with the appended claims all such modifications and equivalents.

I claim:

1. A system for generating an astigmatism-corrected beam having an elliptical cross-section shape emitted from a low-level laser therapy device, the system comprising:
   a laser diode for generating a first beam with an elliptical cross section having a low-divergence minor axis and a high-divergence major axis;
   a first-divergence cylindrical lens which increases a divergence of the low-divergence minor axis toward the divergence of the high-divergence major axis, the cylindrical lens thereby transmitting a second beam with a second elliptical cross section; and
   a first collimating lens for receiving and collimating the second beam;
   wherein the collimating lens emits an emitted beam having an emitted beam elliptical cross section with a minor axis length and a major axis length, and wherein the ratio of the major axis length to the minor axis length is less than 2:1.

2. The system according to claim 1, wherein the first beam has an initial beam elliptical cross section with a minor axis length and a major axis length, and wherein the ratio of the initial beam elliptical cross section major axis length to the initial beam elliptical cross section minor axis length is at least 4:1.

3. The system according to claim 1, wherein the first collimating lens has an elliptical cross section.

4. The system according to claim 1, wherein the first collimating lens is interchangeable with another collimating lens, and wherein when another collimating lens is employed the emitted beam exhibits a different aperture and power density.

5. The system according to claim 1, wherein the cylindrical lens and the collimating lens have anti-reflection coating corresponding to a wavelength band of the laser diode.

6. The system according to claim 1, wherein at least one of the cylindrical lens and the collimating lens are fabricated with injection molded plastic.

7. A method for generating an astigmatism-corrected beam having an elliptical cross-section shape emitted from a low-level laser therapy appliance, the method comprising:
   generating with a laser diode a first beam with an elliptical cross section having a low-divergence minor axis and a high-divergence major axis;
   increasing with a first-divergence cylindrical lens a divergence of the low-divergence minor axis toward the divergence of the high-divergence major axis, thereby transmitting with the cylindrical lens a second beam with a second elliptical cross section;
   receiving and collimating the second beam with a first collimating lens; and
   emitting with the collimating lens, and from the low-level laser therapy appliance, an emitted beam having an emitted beam elliptical cross section with a minor axis length and a major axis length, and wherein the ratio of the major axis length to the minor axis length is less than 2:1.

8. The method according to claim 7, wherein generating the first beam comprises generating the first beam with an initial beam elliptical cross section with a minor axis length and a major axis length, and providing the ratio of the initial beam elliptical cross section major axis length to the initial beam elliptical cross section minor axis length to be at least 4:1.

9. The method according to claim 7, further comprising providing the first collimating lens with an elliptical cross section.

10. The method according to claim 7, further comprising interchanging the first collimating lens with another collimating lens, wherein when employing the another collimating lens the emitted beam exhibits a different aperture and power density.

11. The method according to claim 7, further comprising providing the cylindrical lens and the collimating lens with an anti-reflection coating corresponding to a wavelength band of the laser diode.

12. The method according to claim 7, further comprising fabricating at least one of the cylindrical lens and the collimating lens with injection molded plastic.

* * * * *